United States Patent [19]
Petrillo, Jr.

[11] 4,168,267
[45] Sep. 18, 1979

[54] PHOSPHINYLALKANOYL PROLINES

[75] Inventor: Edward W. Petrillo, Jr., Pennington, N.J.

[73] Assignee: E. R. Squibb & Sons, Inc., Princeton, N.J.

[21] Appl. No.: 953,711

[22] Filed: Oct. 23, 1978

[51] Int. Cl.² .................................. C07D 207/16
[52] U.S. Cl. .................... 260/326.2; 260/326.47; 260/936; 260/941; 260/946; 424/274
[58] Field of Search .................... 260/326.47, 326.2

[56] References Cited
U.S. PATENT DOCUMENTS

| 4,046,889 | 9/1977 | Ondetti et al. | 260/326.47 |
| 4,077,964 | 3/1978 | Secolier et al. | 260/326.4 |

Primary Examiner—Donald G. Daus
Assistant Examiner—Mary C. Lee
Attorney, Agent, or Firm—Lawrence S. Levinson; Merle J. Smith; Stephen B. Davis

[57] ABSTRACT

New phosphinylalkanoyl prolines which have the general formula

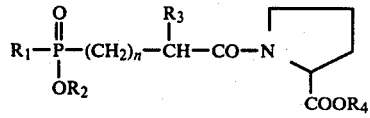

wherein
$R_1$ is lower alkyl, phenyl or phenyl-lower alkyl;
$R_2$ is hydrogen, phenyl-lower alkyl or a metal ion;
$R_3$ is hydrogen or lower alkyl;
$R_4$ is hydrogen, lower alkyl, phenyl-lower alkyl or a metal ion; and
n is 0 or 1,
are useful as hypotensive agents.

24 Claims, No Drawings

PHOSPHINYLALKANOYL PROLINES

SUMMARY OF THE INVENTION

This invention relates to new phosphinylalkanoyl prolines which have the formula $$R_1-\underset{\underset{OR_2}{|}}{\overset{\overset{O}{\|}}{P}}-(CH_2)_n-\underset{\underset{*}{|}}{\overset{\overset{R_3}{|}}{C}H}-CO-N\underset{\underset{COOR_4}{|}}{\overset{\overset{H_2C-CH_2}{|\quad\quad|}}{\diagdown\quad\diagup}}\overset{CH_2}{\underset{CH}{|}} \quad (I)$$

$R_1$ is lower alkyl, phenyl or phenyl-lower alkyl;
$R_2$ is hydrogen, phenyl-lower alkyl or a metal ion;
$R_3$ is hydrogen or lower alkyl;
$R_4$ is hydrogen, lower alkyl, phenyl-lower alkyl or a metal ion; and
n is 0 or 1.

DETAILED DESCRIPTION OF THE INVENTION

In formula I, the lower alkyl groups represented by the symbols are straight or branched chain aliphatic hydrocarbon groups having up to seven carbon atoms, for example, methyl, ethyl, propyl, isopropyl, butyl, sec.butyl, t-butyl and the like. The $C_1$–$C_4$ members and especially the $C_1$–$C_2$ members are preferred. The phenyl-lower alkyl groups are aralkyl radicals of the same type, phenylmethyl and phenylethyl being preferred, especially phenylmethyl.

The metal ions represented by $R_2$ and $R_4$ are monovalent metal ions, preferably the alkali metal ions, especially sodium, potassium and lithium.

Preferred embodiments of this invention are those compounds of formula I wherein n is 0 or 1, especially 0; $R_1$ is phenyl or phenyl-lower alkyl, especially phenyl-$C_1$–$C_3$-alkyl; $R_2$ is hydrogen or phenyl-lower alkyl, especially hydrogen or phenylmethyl; $R_3$ is hydrogen or lower alkyl, especially hydrogen or methyl; and $R_4$ is hydrogen or alkali metal, especially hydrogen, sodium, potassium or lithium.

The compounds of this invention are produced by reacting proline, preferably in the form of a lower alkyl or phenyl-lower alkyl ester in which the ester group is easily removed, e.g., the t-butyl ester, phenylmethyl ester or the like, with a phosphinyl-acetic acid of the formula $$R_1-\underset{\underset{OR_2}{|}}{\overset{\overset{O}{\|}}{P}}-(CH_2)_n-\overset{\overset{R_3}{|}}{C}H-COOH \quad (II)$$

when n is 0, in the presence of a condensing agent like 1,1'-carbonyl-diimidazole or dicyclohexylcarbodiimide and in an inert organic solvent like acetonitrile, dichloromethane, ether, tetrahydrofuran, dioxane or the like or with a phospholane of the formula $$R_1-\underset{\underset{O\rule{1cm}{0.4pt}C=O}{|}}{\overset{\overset{O}{\|}}{P}}-CH_2-\overset{\overset{R_3}{|}}{C}H \quad (III)$$

when n is 1, in the presence of a base like triethylamine, pyridine, N,N-dimethylamine or the like in an inert organic solvent like those mentioned above.

When $R_2$ or $R_4$ is phenylmethyl, this group can be converted to hydrogen by catalytic reduction, e.g., with palladium on carbon or palladium on barium sulfate according to conventional methods.

When $R_4$ is an easily removable ester group like t-butyl, treatment of the ester with trifluoroacetic acid and anisole yields the free acid, i.e., $R_4$ is hydrogen. When $R_2$ is lower alkyl, treatment with a halosilane such as bromotrimethylsilane or iodotrimethylsilane and then water yields the free acid.

The acids form metal salts with monovalent metals like alkali metal salts by treatment with a metal hydroxide, e.g., in aqueous solution, according to conventional methods.

The proline esters are produced by any of a variety of known esterification methods utilizing a lower alkanol, or phenyl-lower alkanol $R_4OH$ (particularly in peptide syntheses) as illustrated in U.S. Pat. No. 4,046,889, Sept. 6, 1977; *J. Org. Chem.* 28, 176 (1963); Pettit, *Synthetic Peptides,* Vol. 3 (Academic Press, 1975), pages 17 to 24; Bodanszky et al., *Peptide Synthesis,* 2nd ed. (Wiley & Sons, 1976), pages 49 to 56; Greenstein et al., *Chemistry of the Amino Acids,* Vol. 2 (Wiley & Sons, 1961), page 782 et seq.; *J. Chromatog* 44, 269 (1969); and sources cited therein. Preferred are those compounds wherein the proline portion of the molecule is in the L-form. When $R_3$ is lower alkyl, the carbon atom to which it is attached is asymmetric so that stereoisomeric or racemic mixtures thereof occur. Here the D-isomeric form is preferred.

The starting materials of formula II can be produced by various methods.

For example, a Grignard reagent $R_1$-MgBr is made to react with a dialkylhalophosphite having the formula $$\text{hal-P}\underset{\diagdown}{\overset{\diagup}{}}\begin{matrix}\text{O-lower alkyl}\\\text{O-lower alkyl}\end{matrix} \quad (IV)$$

wherein hal represents halogen, preferably chlorine or bromine, to obtain a compound having the formula $$R_1-\text{P}\underset{\diagdown}{\overset{\diagup}{}}\begin{matrix}\text{O-lower alkyl}\\\text{O-lower alkyl}\end{matrix} \quad (V)$$

Reaction of this compound with a haloacyl ester having the formula $$\text{hal}-\overset{\overset{R_3}{|}}{C}H-COO\text{-lower alkyl} \quad (VI)$$

produces a compound having the formula $$R_1-\underset{\underset{O\text{-lower alkyl}}{|}}{\overset{\overset{O}{\|}}{P}}-\overset{\overset{R_3}{|}}{C}H-COO\text{-lower alkyl} \quad (VII)$$

which is then hydrolyzed with aqueous acid, e.g., hydrochloric acid, to convert it to the phosphinylacetic acid having the formula

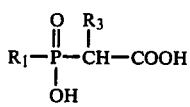

(VIII)

The latter is then esterified with methanol and acetyl chloride or the like and treated with benzyl p-tolyltriazene to convert it to the phenylmethyl ester having the formula

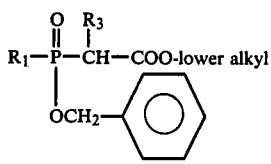

(IX)

Alternatively the compound of formula VII is treated with trimethylsilyl bromide and benzyl-p-tolyl triazene to convert it to the compound of formula IX.

The latter is then hydrolyzed with base, e.g., sodium hydroxide, to obtain the starting material having the formula

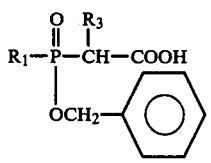

(X)

Alternatively, when $R_1$ is lower alkyl or phenyl, an alkylphosphinic acid having the formula

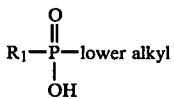

(XI)

is converted with phosphorus pentachloride to the chloride having the formula

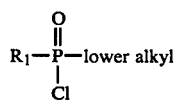

(XII)

and then to the aralkyl derivative with an aralkanol like benzyl alcohol

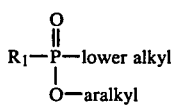

(XIII)

Treatment of this product with a lithium dialkylamide like lithium diisopropylamide or an alkyllithium like sec-butyllithium and carbon dioxide yields the product having the formula

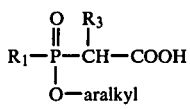

(XIV)

As a further alternative, when $R_1$ is lower alkyl or phenyl-lower alkyl, the compound of formula XIV wherein $R_1$ is methyl can be esterified with diazomethane or the like to obtain a compound having the formula

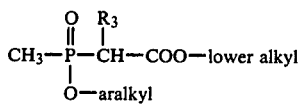

(XV)

and then this compound is treated with a lithium dialkylamide like lithium diisopropylamide and an alkyl halide or aralkyl halide $R^1$-hal wherein $R^1$ is lower alkyl or phenyl-lower alkyl, to obtain the product having the formula

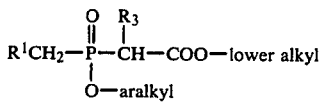

(XVI)

The lower alkyl ester can then be converted by conventional methods, e.g., with sodium hydroxide to obtain the free acid.

The starting materials of formula III are produced by the general methods illustrated in Zh. Obsh. Kim. 37, 411 (1967) and 38, 288 (1968).

Additional experimental details are provided by the illustrative examples below.

The compounds of this invention are angiotensin converting enzyme inhibitors and are useful as hypotensive agents, particularly for the reduction of renin-angiotensin related hypertension, for example, renovascular hypertension and malignant hypertension. By administering a composition containing one or a combination of angiotensin converting enzyme inhibitors of this invention to a hypertensive mammal, it intervenes in the renin→angiotensinogen→angiotensin I→angiotensin II sequence and the hypertension is reduced or alleviated.

A single dose, or preferably two to four divided daily doses, provided on a basis of 30 to 300 mg. per kilogram per day and especially about 10 to 100 mg. per kilogram per day is appropriate to bring about a reduction in elevated blood pressure. The animal model experiments described by Engel., Proc. Soc. Exp. Biol. Med. 143, 483 (1973) provide a valuable guide.

The composition is preferably administered subcutaneously, intramuscularly, intravenously or intraperitoneally, but it can also be administered orally with a dose of 10-1000 mg. per kilogram per day, preferably about 10 to 100 mg. per kilogram per day. The compound or compounds of formula I can be formulated as tablets, capsules or elixirs for oral administration. Sterile solutions or suspensions can be used for parenteral use.

About 100 to 500 mg. of a compound or compounds of formula I can be compounded with a physiologically acceptable vehicle, carrier, excipient, binder, preservative, stabilizer, flavor, etc., in a conventional unit dosage form as called for by accepted pharmaceutical practice. The amount of active substance is selected so as to provide a dosage in the range indicated.

The following examples are illustrative of the invention and represents preferred embodiments. All temperatures are in degrees Celsius.

EXAMPLE 1

[Hydroxy(3-phenylpropyl)phosphinyl]acetic acid (a) Magnesium metal (4.86 g., 0.2 moles) is slurried in diethylether (100 ml.) and treated dropwise with a solution of 3-bromopropylbenzene 39.8 g., 0.2 moles) in diethyl ether (100 ml.). Addition is adjusted so as to cause gentle refluxing of the reaction mixture. After the addition is complete, the reaction mixture is stirred at room temperature overnight. The mixture is filtered under nitrogen and added dropwise to a chilled (0°) solution of diethylchlorophosphite (31.3 g., 0.2 moles) in diethyl ether (60 ml.) so as to keep the internal temperature below 10°. After the addition is complete, the reaction mixture is heated at reflux for one hour. The mixture is then chilled, filtered and concentrated in vacuo. The residue is distilled in vacuo to yield 19 g. of (3-phenylpropyl)phosphonous acid, diethyl ester, b.p. 90°–92°/0.05 mm.

(b) A mixture of methylbromoacetate (9.33 g., 0.06 moles) and (3-phenylpropyl)phosphonous acid, diethyl ester (2.16 g., 0.009 moles) is heated at 140° until distillation of ethyl bromide begins. An additional amount of the phosphonous acid ester (8.64 g., 0.036 moles) is then added dropwise over 10 minutes. After addition is complete, the reaction mixture is heated at 140° for an additional 45 minutes. The reaction mixture is then cooled to 100° and concentrated in vacuo to remove excess methyl bromoacetate and unreacted starting material. TLC (EtOAc) and NMR indicates the product [ethoxy(3-phenylpropyl)phosphinyl]acetic acid, methyl ester is >90% pure, yield 11.8 g.). This material is used in the next step without further purification.

(c) A mixture of [ethoxy(3-phenylpropyl)phosphinyl]acetic acid, methyl ester (3 g., 0.0106 moles) in 6N hydrochloric acid (25 ml.) is heated at reflux for 6 hours, then the reaction mixture is concentrated in vacuo. The resultant solid is recrystallized twice from ethyl acetate/benzene to yield 1.5 g. of [hydroxy(3-phenylpropyl)phosphinyl]acetic acid, m.p. 118°–119°.

EXAMPLE 2

[Hydroxy(2-phenylethyl)phosphinyl]acetic acid (a) Magnesium metal (4.86 g., 0.2 moles) is slurried in diethyl ether (100 ml.) and treated dropwise with a solution of 2-bromoethylbenzene (37 g., 0.2 moles) in diethyl ether (100 ml.). Addition is adjusted so as to cause gentle refluxing of the reaction mixture. After addition is complete, the reaction mixture is stirred at room temperature overnight. The mixture is filtered under nitrogen and added dropwise to a chilled (0°) solution of diethylchlorophosphite (31.3 g., 0.2 moles) in diethyl ether (60 ml.) so as to keep the internal temperatures below 10°. After addition is complete, the reaction mixture is heated at reflux for one hour. The mixture is then chilled, filtered and concentrated in vacuo. The residue is distilled in vacuo to yield 20 g. of (2-phenylethyl)phosphonous acid diethyl ester, b.p. 90°–92°/0.05 mm.

(b) A mixture of methylbromoacetate (9.33 g., 0.06 moles) and (2-phenylethyl)phosphonous acid diethyl ester (2.54 g., 0.011 moles) is heated at 140° until distillation of ethyl bromide begins. An additional amount of starting material (7.63 g., 0.034 moles) is then added dropwise over 10 minutes. After addition is complete, the reaction mixture is heated at 140° for an additional one hour. The reaction mixture is then cooled to 100° and concentrated in vacuo to remove excess starting materials. TLC (EtOAc) and NMR indicates the product is >90% pure, yield 11 g. The product [ethoxy(2-phenylethyl)phosphinyl]acetic acid, methyl ester is used without further purification.

(c) A mixture of [ethoxy(2-phenylethyl)phosphinyl]acetic acid, methyl ester (3 g., 0.011 moles) in 6 N hydrochloric acid (25 ml.) is heated at reflux for 6 hours, then concentrated in vacuo. The resultant solid is recrystallized twice from ethyl acetate/benzene to yield 2.3. g. of [hydroxy[2-phenylethyl]phosphinyl]acetic acid, m.p. 120°–121°.

EXAMPLE 3

Dimethylphosphinic acid, phenylmethyl ester (a) A suspension of tetramethylbiphosphine bisulfide (25 g., 0.134 moles) in carbon tetrachloride (150 ml.) is heated to reflux, with stirring, and 30% hydrogen peroxide (46 ml., 0.4 moles) is added dropwise (40 minutes). Following the addition, reflux is continued for 5 hours. After cooling, the aqueous layer is removed, millipore filtered, and concentrated in vacuo. The residue is dissolved in refluxing benzene (one liter); water remaining in the mixture is removed by azeotropic distillation. After filtration of the hot solution and cooling, 19 g. (75%) of the product, dimethylphosphinic acid, m.p. 82°–84°, is removed.

(b) The portionwise addition of dimethylphosphinic acid (22.6 g., 0.024 moles) to phosphorus pentachloride (50 g., 0.24 moles) results in the formation of a liquid mixture, accompanied by a vigorous, exothermic reaction. Following the addition, the mixture is heated at 115° for one hour before being subjected to vacuum distillation to give 24.3 g. (90%) of a low melting solid, dimethylphosphinyl chloride, b.p. 82° at 0.5 mm. pressure.

(c) To a cooled (0°) solution of dimethylphosphinyl chloride (3.4 g., 0.03 moles) in dichloromethane (50 ml.) is added dropwise (over a period of 20 minutes), with stirring, a solution of benzyl alcohol (3.2 g., 0.03 moles) and triethylamine (3.4 g., 0.03 moles) in dichloromethane (30 ml.). After stirring at 0° for one hour, and at ambient temperature overnight, the mixture is filtered and the filtrate is concentrated in vacuo. The residue (5 g., 90%) becomes semi-solid at room temperature. It is recrystallized from pentane (450 ml.) with a recovery of dimethylphosphinic acid, phenylmethyl ester, yield 3.6 g. (65%) m.p. 41°–45°. A second recrystallization of 0.5 g. from pentane (75 ml.) gives a recovery of 0.26 g. of product, m.p. 46°–47°.

EXAMPLE 4

(Hydroxymethylphosphinyl)acetic acid (a) A solution of 0.0272 moles of lithium diisopropylamide in tetrahydrofuran is prepared by the dropwise addition of N-butyllithium (12.3 ml. of a 2.22 N hexane solution, 0.0272 moles) to diisopropylamine (5.5 g., 0.0544 moles) in a cooled (0°) solution of hexane (70 ml.). The solvent is removed in vacuo and replaced by tetrahydrofuran (80 ml.). The solution is cooled to −76° and a solution of dimethylphosphinic acid, phenylmethyl ester (2.5 g., 0.0136 moles) in tetrahydrofuran (50 ml.) is added over a period of 3–4 minutes. After stirring for 20 minutes, dry carbon dioxide is passed into the mixture for 30 minutes, the cooling bath is removed, and the solution, at room temperature, is diluted with ether (150 ml.). It is extracted with water (2×60 ml.).

The aqueous phase (pH ca. 10) is washed with ether (25 ml.) and acidified to a pH of 1 with hydrochloric acid. The acidic solution is extracted with dichloromethane (9×100 ml.). After washing with brine, and drying over magnesium sulfate, the dichloromethane solution is concentrated in vacuo to give an oil (2.4 g.). The oil is dissolved in dichloromethane (100 ml.). The solution is extracted with saturated sodium bicarbonate solution (3×25 ml.). After the alkaline solution is washed with dichloromethane (4×50 ml.) it is acidified to a pH of 1 with hydrochloric acid. The acidic solution is extracted with dichloromethane (10×57 ml.). After washing with brine and drying over magnesium sulfate, the solvent is removed in vacuo to give 2.2 g. (84%) of product [methyl(phenylmethoxy)phosphinyl]acetic acid. TLC, silica gel, CH$_2$Cl$_2$/MeOH/HOAc (8:1:1) shows a single spot, R$_f$=0.70.

(b) A mixture of [methyl(phenylmethoxy)phosphinyl]acetic acid (0.5 g., 0.022 moles) and 5% palladium on carbon (25 mg.) in methanol (50 ml.) is stirred vigorously under one atmosphere of hydrogen until 39 ml. of hydrogen has been consumed. The mixture is filtered through diatomaceous earth and concentrated in vacuo. The residue (0.37 g.) solidifies after trituration with pentane, m.p. 44°–48°. It is recrystallized from ethyl acetate (15 ml.) with a recovery of 0.17 g. (57%) of (hydroxymethylphosphinyl)acetic acid, m.p. 87°–88°.

EXAMPLE 5

[(Phenylmethoxy)-(2-phenylethyl)phosphinyl]acetic acid, methyl ester (a) A solution of [methyl(phenylmethoxy)phosphinyl]acetic acid in ethyl acetate-ether is treated with an excess of diazomethane in ether and stirred for three hours. The excess diazomethane is destroyed by the addition of acetic acid. The solution is washed with sodium bicarbonate and brine, dried over magnesium sulfate, and evaporated to give an 87% yield of [methyl(phenylmethoxy)phosphinyl]acetic acid, methyl ester as a clear oil (TLC R$_f$=0.18 (ethyl acetate)).

(b) A solution of [methyl(phenylmethoxy)phosphinyl]acetic acid, methyl ester (1.0 gm., 0.004 mole) in 20 ml. of tetrahydrofuran is added over 50 minutes to a solution of lithium diisopropylamide (0.008 mol.) in tetrahydrofuran maintained at −78° under argon. Following the addition, stirring is continued at −78° for 20 minutes. Phenylmethyl bromide (0.684 gm., 0.004 mol.) in tetrahydrofuran (5 ml.) is then added and the mixture is stirred for 2 hours at −78° and for one hour at 0°. The mixture is then neutralized to pH5 with acetic acid and poured into ether. The ether layer is washed with water, 5% potassium bisulfate and brine, and dried over magnesium sulfate. Evaporation in vacuo yields a residue which is chromatographed on silica gel with dichloromethane/ethyl acetate. The product, [(2-phenylethyl)(phenylmethoxy)phosphinyl]acetic acid, methyl ester (0.66 gm., 50%) is identical by TLC and NMR to that prepared in Example 6.

EXAMPLE 6

(1-[[Hydroxy-(2-phenylethyl)phosphinyl]acetyl]-L-proline (a) A solution of (1-[hydroxy-(2-phenylethyl)phosphinyl]acetic acid (9.1 g., 0.04 moles) and acetyl chloride (1 ml.) in methanol (100 ml.) is heated at reflux overnight. The reaction mixture is then concentrated in vacuo to yield 9.63 g. of product, [hydroxy-(2-phenylethyl)phosphinyl]acetic acid, methyl ester.

(b) A chilled (0°) solution of 3-benzyl-1-p-tolyl triazene (8.91 g., 0.04 moles) in diethyl ether (350 ml.) is treated all at once with a solution of [hydroxy(2-phenylethyl)phosphinyl]acetic acid, methyl ester (9.63 g., 0.04 moles) in ethyl acetate (15 ml.). The reaction mixture is then stirred at room temperature for 4 hours. The ether solution is then extracted with 10% hydrochloric acid and brine, dried over magnesium sulfate and concentrated in vacuo. The residue is chromatographed on silica gel [silicAR CC-7] (500 ml.) eluting with mixtures of hexane/ethyl acetate to yield 6 g. of product, [(2-phenylethyl)(phenylmethoxy)phosphinyl]acetic acid, methyl ester, (TLC: silica gel; hexane/ethyl acetate (1:1); R$_f$=0.15; UV visualization).

(c) A solution of [(2-phenylethyl)-(phenylmethoxy)phosphinyl]acetic acid, methyl ester (5.62 g., 0.017 moles) and 1N sodium hydroxide (17.1 ml., 0.017 moles) in methanol (30 ml.) is stirred at room temperature overnight. The reaction mixture is concentrated in vacuo. The residue is dissolved in water and washed with ether. The aqueous layer is then acidified with potassium bisulfate solution and extracted several times with ethyl acetate. The combined ethyl acetate extracts are dried over magnesium sulfate and concentrated in vacuo to yield 5.6 g. of product [(2-phenylethyl)(phenylmethoxy)phosphinyl]acetic acid. (Electrophoresis: 2000 V; 20 minutes, 0.1 M NH$_4$HCO$_3$+4.5 cm.; single spot visualized with carboxyl reagent).

(d) Carbonyl diimidazole (2.86 g., 0.018 moles) is dissolved in acetonitrile (200 ml.), chilled in an ice bath, and treated with [(2-phenylethyl)-(phenylmethoxy)phosphinyl]acetic acid (5.6., 0.018 moles) in acetonitrile (15 ml.). The mixture is stirred at 0° for one hour. The mixture is then treated all at once with a solution of L-proline phenylmethyl ester [produced by the method described in J. Org. Chem. 28, 174 (1963)] (3.6 g., 0.018 moles) in acetonitrile (5 ml.). The reaction mixture is stirred at 0° for one hour, then left at room temperature overnight. The reaction mixture is concentrated in vacuo. The residue is dissolved in ethyl acetate and washed with 5% potassium bisulfate and 5% sodium bicarbonate. The ethyl acetate layer is dried over sodium sulfate and concentrated in vacuo to yield 8.0 g. of crude product. This product is chromatographed on silica gel [silicAR CC-7] (250 ml.) eluting with mixtures of CH$_2$Cl$_2$/EtOAc to yield 7.11 g. of product, 1-[[2-phenylethyl)-(phenylmethoxy)phosphinyl]acetyl]-L-proline, phenylmethyl ester, (TLC silica gel; ethyl acetate; R$_f$=0.2;U.V. visualization).

(e) A mixture of 1-[[(2-phenylethyl)-(phenylmethoxy)phosphinyl]acetyl]-L-proline, phenylmethyl ester (7.11 g., 0.014 moles) and 10% palladium on carbon (800 mg.) in absolute ethanol (400 ml.) is stirred vigorously under one atmosphere of hydrogen until 630 ml. of hydrogen has been consumed. The reaction mixture is filtered through Celite (diatomaceous earth) and concentrated in vacuo. The residue is dissolved in double-distilled water, millipore filtered and lyophilized to yield 4.2 g. of amorphous product, 1-[[hydroxy(2-phenylethyl)phosphinyl]acetyl]-L-proline [α]$_D$=−55, c 18.7 methanol.

EXAMPLE 7

1-[(Hydroxymethylphosphinyl)acetyl]-L-proline (a) Carbonyl diimidazole (1.3 g., 0.0079 moles) is added to a chilled solution (0°) of [methyl(phenylmethoxy)phosphinyl]acetic acid (1.8 g., 0.0079 moles) in acetonitrile (50 ml.), and the mixture is stirred for one hour. It is then treated with a solution of L-proline benzyl ester (1.61 g., 0.0079 moles) in acetonitrile (25 ml.). The reaction mixture is stirred at 0° for one hour, then left at ambient temperature overnight. The reaction mixture is concentrated in vacuo. The residue is dissolved in ethyl acetate (250 ml.), washed with 5% potassium bisulfate and saturated sodium bicarbonate solution, dried over magnesium sulfate, and concentrated in vacuo. The crude product is chromatographed on silica gel (Baker #5-3405, 60-200 mesh, 300 ml.) eluting with mixtures of dichloromethane/ethyl acetate to give 2.4 g. (71%) of product 1-[[methyl(phenylmethoxy)phosphinyl]acetyl]-L-proline, phenylmethyl ester, TLC, silica gel; ethyl acetate: $R_f=0.08$, PMA plus heat visualization.

(b) A mixture of 1-[[methyl(phenylmethoxy)phosphinyl]acetyl]-L-proline, phenylmethyl ester (2.3 g., 0.0052 moles) and 5% palladium on carbon (100 mg.) in absolute methanol (125 ml.) is stirred vigorously under one atmosphere of hydrogen until 190 ml. of hydrogen has been consumed. The reaction mixture is filtered through diatomaceous earth and concentrated in vacuo. The residue is dissolved in double distilled water (75 ml.), millipore filtered, and lyophilized to yield 1.1 g. of amorphous 1-[(hydroxymethylphosphinyl)acetyl]-L-proline. The product is again dissolved in double-distilled water (50 ml.), millipore filtered and 25 one milliliter portions are pipetted into 25 vials and lyophilized to give 21.4 mg. in each vial, for a total of 535 mg.

Analysis calcd. for $C_8H_{14}NO_5P$: C, 40.85; H, 6.00; N, 5.96; P, 13.17,

Found: C, 41.01; H, 6.15; N, 5.88; P, 12.90.

EXAMPLE 8

1-[[Hydroxy-(3-phenylpropyl)phosphinyl]acetyl]-L-proline (a) A solution of [hydroxy(3-phenylpropyl)phosphinyl]acetic acid (3.5 g., 0.015 moles) and acetyl chloride (1 ml.) in methanol (50 ml.) is heated at reflux overnight. The reaction mixture is then concentrated in vacuo to yield 3.02 g. of [hydroxy(3-phenylpropyl)phosphinyl]acetic acid, methyl ester. (Electrophoresis: 2000 V; 20 minutes.; 0.1 M NH₄HCO₃; +5 cm; single spot visualized with carboxyl reagent).

(b) A chilled solution (0°) of 3-benzyl-1-p-tolytriazene (2.65 g., 0.012 moles) in diethyl ether (115 ml.) is treated all at once with a solution of [hydroxy(3-phenylpropyl)phosphinyl]acetic acid, methyl ester (3.02 g., 0.012 moles) in ethyl acetate (10 ml.). The reaction mixture is then stirred at room temperature for four hours. The ether solution is extracted with 10% hydrochloric acid and brine, dried over sodium sulfate, and concentrated in vacuo. The residue is chromatographed on silica gel [silicAR CC-7] (300 ml.) eluting with hexane/ethyl acetate mixtures to yield 2 g. of product [phenylmethoxy)(3-phenylpropyl)phosphinyl]acetic acid, methyl ester (TLC:silica gel; ethyl acetate/hexane (1:1); $R_f=0.15$; UV visualization).

(c) A solution of [(phenylmethoxy) (3-phenylpropyl)phosphinyl]acetic acid, methyl ester (1.9 g., 0.0055 moles) and 1 N sodium hydroxide solution (5.6 ml.) in methanol (20 ml.) is stirred at room temperature overnight. The reaction mixture is concentrated in vacuo. The residue is dissolved in water and washed with ether. The aqueous layer is acidified with potassium bisulfate solution and extracted several times with ethyl acetate. The combined ethyl acetate extracts are dried over magnesium sulfate and concentrated in vacuo to yield 1.8 g. of [(phenylmethoxy)(3-phenylpropyl)phosphinyl]acetic acid. (Electrophoresis: 2000 V; 20 minutes; 0.1 M NH₄HCO₃; +4.5 cm; single spot visualized with carboxyl reagent).

(d) Carbonyl diimidazole (929 mg., 0.0057 moles) is dissolved in acetonitrile (140 ml.), chilled in an ice water bath and treated with [(phenylmethoxy)(3-phenylpropyl)phosphinyl]acetic acid (1.9 g., 0.0057 moles) in acetonitrile (10 ml.). The mixture is stirred at 0° for one hour. The mixture is then treated with a solution of L-proline phenylmethyl ester (1.17 g., 0.0057 moles) in acetonitrile (5 ml.). The reaction mixture is stirred at 0° for one hour then left at room temperature overnight. The reaction mixture is concentrated in vacuo. The residue is dissolved in ethyl acetate, washed with 5% potassium bisulfate and 5% sodium bicarbonate, dried over magnesium sulfate, and concentrated in vacuo. The crude product is chromatographed on silica gel [silicAR CC-7] (100 ml.) eluting with mixtures of $CH_2Cl_2$/EtOAc to yield 2.3 g. of product, 1-[[(phenylmethoxy)(3-phenylpropyl)phosphinyl]acetyl]-L-proline, phenylmethyl ester (TLC:silica gel; ethyl acetate; $R_f=0.2$; UV visualization).

(e) A mixture of 1-[(phenylmethoxy)(3-phenylpropyl)phosphinyl]acetyl-L-proline, phenylmethyl ester (2.3 g., 0.0044 moles) and 10% palladium on carbon (200 mg.) in absolute ethanol (200 ml.) is stirred vigorously under one atmosphere of hydrogen until 200 ml. of hydrogen has been consumed. The reaction mixture is then filtered through diatomaceous earth and concentrated in vacuo. The residue is dissolved in double-distilled water, millipore filtered, and lyophilized to yield 1.4 g. of amorphous 1-[[hydroxy(3-phenylpropyl)phosphinyl]acetyl]-L-proline $[\alpha]_D= -51$ (c, 16.4, methanol).

EXAMPLE 9

1-[3-(Hydroxyphenylphosphinyl)-1-oxopropyl]-L-proline (a) Methanol (12.8 gm., 0.4 mol.) and triethylamine (40.4 gm., 0.4 mol.) are dissolved in 750 ml. ether and chilled in an ice bath. Phenyl dichlorophosphine (35.8 gm., 0.2 mol.) is added dropwise and the reaction mixture is stirred overnight. The resulting suspension is filtered and the filtrate concentrated to an oil which is distilled in vacuo to give the product, phenylphosphonous acid dimethyl ester, b.p. 100°-105°/10 mm; yield 20 gm. (59%).

(b) Phenyldichlorophosphine (8.95 gm., 0.05 mol.) is dissolved in 50 ml. ether chilled in ice bath under argon. Phenylphosphonous acid, dimethyl ester (8.50 gm., 0.05 mol.) in 20 ml. ether is added dropwise and the mixture stirred 2 hours. The solution is concentrated in vacuo and the residue distilled to give 8.5 gm. (49%) of phenylphosphonochloridous acid methyl ester, b.p. 66°/0.6 mm.

(c) Phenylphosphonochloridous acid, methyl ester (8.5 gm., 0.049 mol.) is treated dropwise with acrylic acid (3.4 ml., 0.049 mol.) under argon at such a rate that the temperature does not exceed 60°. After the exothermic reaction has subsided, a portion (2.6 gm.) of the resulting clear glass is subjected to Kugelrohr distillation at 0.005 mm. As the bath temperature reaches 160°, a volatile liquid distills. Further heating to 240° gives a main fraction, 2,5-dioxo-2-phenyl-1,2-oxaphospholane, total 1.35 gm. (65.%), as a glassy solid.

(d) L-Proline 1,1-dimethylethyl ester (1.18 gm., 0.0069 mol.) and triethylamine (0.95 ml., 0.0069 mol.) are dissolved in 30 ml. dichloromethane and cooled in an ice bath. The product of part c (1.35 gm., 0.0069 mol.) in 10 ml. of dichloromethane is added dropwise and the mixture stirred overnight. The resulting solution is evaporated to a residue which is taken up in water and applied to a 2.5×60 cm. column of AG-50 ion exchange resin (H+ form). Elution with water gives a main fraction which is lyophilized to an amorphous white solid, 1-[3-(hydroxyphenylphosphinyl)-1-oxopropyl]-L-proline, 1,1-dimethyl ethyl ester, total 1.40 gm. (55%). TLC: $R_f=0.53$, silica, butanol/acetic acid/water, 3:1:1. Electrophoresis: single spot +3,0 cm., 2000V, mA 35, pH 6.5, 30 minutes.

(e) 1-[3-(Hydroxyphenylphosphinyl)-1-oxopropyl]-L-proline, 1,1-dimethylethyl ester (1.40 gm., 0.0038 mol.) is dissolved in 20 ml. trifluoroacetic acid and 5ml. anisole and stirred 1 hour. The acid is removed in vacuo and the residue triturated several times with ether/hexane. The residue is taken up in water and the solution washed with ether, millipore filtered and lyophilized. The resulting foam is crystallized from ethyl acetate to give 1-[3-(hydroxyphenylphosphinyl)-1-oxopropyl]-L-proline m.p., 125°–128°, total 300 mg. (25%).

EXAMPLE 10

1-[(Hydroxyphenylphosphinyl)acetyl]-L-proline (a) A solution of phenylphosphonous acid, dimethyl ester (15.6 g., 0.09 mol.) and methyl iodide (3 ml.) in benzene (75ml.) is heated at reflux for 2 hours. The mixture is filtered and the filtrate is concentrated in vacuo to give a liquid residue of 15.2 g. (97%). An NMR spectrum shows the presence of two separate doublets, each equivalent to one methyl group. The product, methylphenylphosphinic acid methyl ester is used without further purification for the following reaction.

(b) Trimethylsilylbromide (15 ml., 0.1 mole) is added portionwise to methylphenyl phosphinic acid, phenethyl ester (15.2 g.,0.1 mole) at a rate to maintain reflux temperature. Following the addition, the mixture is stirred one hour at ambient temperature. The volatiles are removed in vacuo. The addition of water (10 ml.) to the liquid residue (20.6 g.) results in the separation of a white solid. The mixture is stirred at ambient temperature overnight, followed by filtration, with a recovery of 14 g. of solid. It is recrystallized from dichloromethane (80 ml.) to give methylphenylphosphinic acid, 9.9 g. (72%), m.p. 133°–135°.

(c) A chilled (0°) solution of 3-benzyl-1-p-tolyl triazine (12.5 g., 0.056 moles) in diethyl ether (150 ml.) is added dropwise, over a period of 45 minutes, to a stirred suspension of methylpherylphosphinic acid (8 g., 0.051 moles) in ethyl acetate (250 ml.). After stirring at room temperature for 3 hours, the mixture is washed with saturated sodium bicarbonate solution, 5% potassium bisulfate, and brine. After drying over magnesium sulfate, the ethereal solution is concentrated in vacuo to give an oil residue of 14.3 g. It is chromatographed on silica gel eluting with mixtures of dichloromethane/ethyl acetate to give 9.25 g. (74%) of methylphenylphosphinic acid, phenylmethyl ester. TLC: silica gel, dichloromethane/ethyl acetate (1:1), $R_f=0.18$, visualized with PMA plus heat.

(d) A solution of 0.033 moles of lithium diisopropylamide is prepared by the dropwise addition of N-butyllithium (15 ml. of a 2.22 N hexane solution, 0.033 moles) to dissopropylamine (4.1 g., 0.067 moles) in a cooled (0°) solution of hexane (70 ml.). The solvent is removed in vacuo and replaced by tetrahydrofuran (85 ml.). The solution is cooled to −76° and a solution of methylphenylphosphinic acid, phenylmethyl ester (4.1 g., 0.0166 mol., 1 equivalent) in tetrahydrofuran (50 ml.) is added over a period of 5 minutes. After stirring for 20 minutes, dry carbon dioxide is passed into the mixture for 30 minutes. The cooling bath is removed, and the solution, at room temprature, is diluted with ether (100 ml.). It is extracted with (125 ml., in 2 portions). The aqueous phase (pH10) is washed with ether (25 ml.), and acidified to a pH of 1 with hydrochloric acid. An oil separates from the acidic solution. It is extracted into dichloromethane (2×100 ml.), washed with brine, dried (MgSO₄), filtered, and the solvent is removed to give the product, [phenyl(phenylmethoxy)phosphinyl]acetic acid as an oil (3.85 g., 77.6%). TLC, silica gel, dichloromethane/ethyl acetate/acetic acid (8:1:1), one spot, $R_f=0.85$ (PMA plus heat visualization).

(e) Carbonyl diimidazole (2.28 g., 0.014 moles) is added to a cooled solution (0°) of [phenyl(phenylmethoxy)phosphinyl]acetic acid (4.2 g., 0.014 moles) in acetonitrile (200 ml.). The mixture is stirred for one hour and a solution of L-proline phenylmethyl ester (2.85 g., 0.014 moles) in acetonitrile (20 ml.) is added all at once. The mixture is stirred an additional hour at 0°, then overnight at ambient temperature. The solvent is removed in vacuo and the residue is dissolved in ethyl acetate (600 ml.) and washed with 5% potassium bisulfate, saturated sodium bicarbonate, and brine. After drying (MgSO₄), the solvent is removed in vacuo to yield 6.7 g. (theory) of crude product. A total of 8 g. of crude product obtained by the above procedure is chromatographed on silica gel (Baker #5-3405, 60–200 mesh, 1200 ml.) eluting with mixtures of CH₂Cl₂/EtOAc to yield 7.0 g. of product 1-[[phenyl(phenylmethoxy)phosphinyl]acetyl]-L-proline, phenylmethyl ester (83%) as an oil. TLC: silica gel, ethyl acetate, $R_f=0.16$, PMA plus heat visualization.

(f) A mixture of 1-[phenyl(phenylmethoxy)phosphinyl]acetyl]-L-proline, phenylmethyl ester (3 g., 0.006 moles) and 5% palladium on carbon (100 mg.) in absolute methanol is stirred vigorously under one atmosphere of hydrogen until 226 ml. of hydrogen has been consumed. The reaction mixture is filtered through diatomaceous earth and concentrated in vacuo. The residue is dissolved in double distilled water, millipore filtered, and lyophilized to yield 1.7 g. (94%) of 1-[(hydroxyphenylphosphinyl)acetyl]-L-proline as an amorphous solid $[\alpha]_D = -65$ (c 11.5, methanol).

EXAMPLE 11

1-[(Ethylhydroxyphosphinyl)acetyl]-L-proline (a) Substitution of methyl iodide for the phenylmethyl bromide in the procedure of Example 5, part b yields [ethyl(phenylmethoxy)phosphinyl]acetic acid, methyl ester. (b) Substitution of [ethyl(phenylmethoxy)phosphinyl]acetic acid, methyl ester for the [(2-phenylethyl)(phenylmethoxy)phosphinyl]acetic acid, methyl ester in the procedure of Example 6, part c yields [ethyl(phenylmethoxy)phosphinyl]acetic acid.

(c) Substitution of [ethyl)phenylmethoxy)phosphinyl]acetic acid for the [(2(phenylmethoxy)phosphinyl]acetic acid in the procedure of Example 6, part d yields 1-[[ethyl(phenylmethoxy)phosphinyl]acetyl]-L-proline, phenylmethyl ester.

(d) Substitution of 1 -[[ethyl(phenylmethoxy)phosphinyl]acetyl]-L-proline, phenylmethyl ester for the 1-[[(2-phenyl)(phenylmethoxyl)phosphinyl]acetyl]-L-proline, phenylmethyl ester in the procedure of Example 6, part e yields 1-[(ethylhydroxyphosphinyl)acetyl]-L-proline.

EXAMPLE 12

1-[(Butylhydroxyphosphinyl)acetyl]-L-proline (a) Substitution of 1-propyl iodide for the phenylmethyl bromide in the procedure of Example 5, part b, yields [butyl(phenylmethoxy)phosphinyl] acetic acid, methyl ester.

(b) Substitution of [butyl(phenylmethoxy)phosphinyl]acetic acid, methyl ester for [2-phenylethyl)(phenylmethoxy)phosphinyl]acetic acid methyl ester in the procedure of Example 6, part c, yields [butyl(phenylmethoxy)phosphinyl] acetic acid.

(c) Substitution of [butyl(phenylmethoxy)phosphinyl]acetic acid for [(2-phenylethyl(phenylmethoxy)phosphinyl]acetic acid in the procedure of Example 6, part d yields 1-[[butyl(phenylmethoxy)phosphinyl]acetyl]-L-proline, phenylmethyl ester.

(d) Substitution of 1-[[butyl(phenylmethoxy)phosphinyl]acetyl]-L-proline, phenylmethyl ester for 1-[[(2-phenylethyl)(phenyl-methoxy)phosphinyl]acetyl-L-proline, phenyl-methyl ester in Example 6, part e, yields 1-[[butylhydroxyphosphinyl]acetyl]-L-proline.

EXAMPLE 13

1-[[Phenyl(2-phenylethoxy)phosphinyl]acetyl]-L-proline (a) Substitution of methylphenyl phosphinyl chloride for dimethylphosphinyl chloride and of phenethyl alcohol for benzyl alcohol in the procedure of Example 3, part c, yields methylphenylphosphinic acid, 2-phenylethyl ester.

(b) Substitution of methylphenylphosphinic acid, 2-phenylethyl ester for methylphenylphosphinic acid, phenylmethyl ester in the procedure of Example 10, part d yields [phenyl(2-phenylethoxy)phosphinyl]acetic acid.

(c) Substitution of [phenyl(2-phenylethoxy)phosphinyl]acetic acid for [phenyl(phenylmethoxyl)phosphinyl]acetic acid in the procedure of Example 10, part e, yields 1-[[phenyl(2-phenylethoxy)phosphinyl]acetyl]-L-proline, phenylmethyl ester.

(d) Substitutio of 1-[[phenyl(2-phenylethoxy)phosphinyl]acetyl]-L-proline for 1-[[ phenyl(phenylmethoxy)phosphinyl]acetyl]-L-proline, phenylmethyl ester in the procedure of Example 10, part f, yields 1-[[phenyl(2-phenylethoxy)phosphinyl]acetyl]-L-proline.

EXAMPLE 14

1-[3-(Hydroxymethylphosphinyl)2-methyl-1-oxopropyl]-L-proline (a) Substitution of 2,4-dimethyl-2,5-dioxo-1,2-oxaphospholane [prepared as described in *Zh. Obsh. Khim* 38, 288 (1968)] for 2,5-dioxo-2-phenyl-1,2-oxaphospholane, in the procedure of Example 9, part d yields 1-[3-(hydroxymethylphosphinyl)-2-methyl-1-oxopropyl]-L-proline, 1,1-dimethyl ethyl ester.

(b) Substitution of 1-[3-(hydroxymethylphosphinyl)-2-methyl-1-oxopropyl]-L-proline, 1,1-dimethyl ethyl ester for 1[3-(hydroxyphenylphosphinyl)-1-oxopropyl]-L-proline in the procedure of Example 9, part e yields 1-[3-(hydroxymethylphosphinyl)-2-methyl-1-oxopropyl]-L-proline.

EXAMPLE 15

1-[3-(Hydroxyphenylphosphinyl)-2-methyl-1-oxopropyl]-L-proline (a) Substitution of 4-methyl-2,5-dioxo-2-phenyl-1,2-oxaphospholane [prepared as described in *Zh. Obsh. Khim* 37, 971 (1967)] for 2,5-dioxo-2-phenyl-1,2-oxaphospholane in the procedure of Example 9, part d yields 1-[3-(hydroxyphenylphosphinyl)-2-methyl-1-oxopropyl]-L-proline, 1,1-dimethylethyl ester (b) Substitution of 1-[3-(hydroxyphenylphosphinyl)-2-methyl-1-oxopropyl]-L-proline, 1,1-dimethylethyl ester for 1-[3-(hydroxyphenylphosphinyl)-1-oxopropyl]-L-prolline, 1,1-dimethylethyl ester in the procedure of Example 9, part e yields 1-[3-(hydroxyphenylphosphinyl)-2-methyl-1-oxopropyl]-L-proline.

EXAMPLE 16

1-[[Hydroxy(phenylmethyl)phosphinyl]acetyl]-L-proline, disodium salt (a) Substitution of methyl(phenylmethyl)phosphinic acid [prepared as described in *Chem. Ber.* 94, 3051 (1961)] for methylphenylphosphinic acid in the procedure of Example 10 part c yields, methyl(phenylmethyl)phosphinic acid, phenylmethyl ester.

(b) Substitution of methyl(phenylmethyl)phosphinic acid, phenylmethyl ester for methylphenylphosphinic acid, phenylmethyl ester in the procedure of Example 10 part d, yields [(phenylmethoxy)(phenylmethyl)phosphinyl]acetic acid.

(c) Substitution of [(phenylmethoxy)(phenylmethyl)phosphinyl]acetic acid for [phenyl(phenylmethoxy)phosphinyl]acetic acid in the procedure of Example 10, part 3, yields 1-[[(phenylmethoxy(phenylmethyl)phosphinyl]acetyl]-L-proline, phenylmethyl ester.

(d) Substitution of 1-[[(phenylmethoxy)(phenylmethyl)phosphinyl]acetyl]-L-proline, phenylmethyl ester for 1[[phenyl(phenylmethoxy)phosphinyl]acetyl]-L-proline, phenylmethyl ester in the procedure of Example 10, part f, yields 1-[[hydroxy(phenylmethyl)phosphinyl]acetyl]-L-proline.

(e) 1-[[Hydroxy(phenylmethyl)phosphinyl]acetyl]-L-proline is dissolved in water and treated with two molar equivalents of aqueous sodium hydroxide. The resulting solution is lyophilized to give the product, 1-[[hydroxy(phenylmethyl) phosphinyl]acetyl]-L-proline disodium salt.

EXAMPLE 17

1-[[Hydroxy(2-phenylethyl)phosphinyl]acetyl]-L-proline, 2-phenylethyl ester (a) L-Proline, 2-phenylethyl ester is prepared from L-proline by substituting 2-phenylethyl alcohol for benzyl alcohol in the procedure described in *J. Org. Chem.* 28, 176 (1953). Substitution of L-proline, 2-phenylethyl ester for L-proline benzyl ester in the procedure of Example 6, part d, gives the product, 1-[[(2-phenylethyl)(phenylmethoxy)phosphinyl]acetyl]-L-proline, 2-phenylethyl ester.

(b) Substitution of 1-[[2-phenylethyl)(phenylmethoxy)phosphinyl]acetyl]-L-proline, 2-phenylethyl ester for 1-[[2-phenylethyl(phenylmethoxy)phosphinyl]acetyl]-L-proline, phenylmethyl ester in the procedure of Example 6, part e, yields 1[[hydroxy(2-phenylethyl)phosphinyl]acetyl]-L-proline, 2-phenylethyl ester.

EXAMPLE 18

2-[Hydroxy[3-phenylpropyl]phosphinyl]propanoic acid (a) Substitution of methyl 2-bromopropanoate for methyl bromoacetate in the procedure of Example 1, part b, yields 2-[ethoxy(3-phenylpropyl)phosphinyl]propanoic acid, methyl ester.

(b) Substitution of 2-[ethoxy(3-phenylpropyl)phosphinyl]propanoic acid, methyl ester for [ethoxy(3-phenylpropyl)phosphinyl]acetic acid, methyl ester in the procedure of Example 1, part c yields, 2-[hydroxy(3-phenylpropyl)phosphinyl]propanoic acid.

EXAMPLE 19

1-[2-Hydroxy(3-phenylpropyl)pghosphinyl]-1-oxopropyl]-L-proline (a) Substitution of 2-[hydroxy(3-phenylpropyl)phosphinyl]propanoic acid for [hydroxy(3-phenylpropyl)phosphinyl]acetic acid in the procedure of Example 6, part a yields 2-[hydroxy(3-phenylpropyl)phosphinyl]propanoic acid, methyl ester.

(b) Substitution of 2-[hydroxy(3-phenylpropyl)phosphinyl]propanoic acid, methyl ester for [hydroxy(3-phenylpropyl)phosphinyl]acetic acid, methyl ester in the procedure of Example 6, part b, yields 2-[(phenylmethoxy)(3-phenylpropyl)phosphinyl]propanoic acid, methyl ester.

(c) Substitution of 2-[(phenylmethoxy)(3-phenylpropyl)phosphinyl]propanoic acid, methyl ester for [(phenylmethoxy((3-phenylpropyl)phosphinyl]acetic acid, methyl ester in the procedure of Example 6, part c, yields 2-[(phenylmethoxy)(3-phenylpropyl)phosphinyl]propanoic acid.

(d) Substitution of 2-[(phenylmethoxy(3-phenylpropyl))phosphinyl]propanoic acid for [(phenylmethoxy)(3-phenylpropyl)phosphinyl]acetic acid in the procedure of Example 6, part d yields 1-[2-oxo-2-[(phenylmethoxy)(3-phenylpropyl)phosphinyl]propyl]-L-proline, phenylmethyl ester. (e) Substitution of 1-[1-oxo-2-[(phenylmethoxy)(3-phenylpropyl)phosphinyl]propyl]-L-proline, phenylmethyl ester for 1-[[(phenylmethoxy)(3-phenylpropyl)phosphinyl]acetyl]-L-proline, phenylmethyl ester in the procedure of Example 6, part e yields 1-[2-[hydroxy(3-phenylpropyl)phosphinyl]-1-oxopropyl]-L-proline.

EXAMPLE 20

1-[3-(Hydroxyphenylphosphinyl)-1-oxopropyl-L-proline, ethyl ester

Substitution of L-proline ethyl ester for L-proline 1,1-dimethylethyl ester in the procedure of Example 9, part d yields, 1-[3-(hydroxyphenylphosphinyl)-1-oxopropyl]-L-proline, ethyl ester.

EXAMPLE 21

1-[3-(Hydroxyphenylphosphinyl)-1-oxopropyl]-L-proline monopotassium salt

1-[3-(Hydroxyphenylphosphinyl)-1-oxopropyl]-L-proline is dissolved in water and treated with one molar equivalent of aqueous potassium hydroxide. The resulting solution is lyophilized to give the product, 1-[3-(hydroxyphenylphosphinyl)-1-oxopropyl]-L-proline, monopotassium salt.

EXAMPLE 22

1-[2-(Hydroxyphenylphosphinyl)-1-oxohexyl]-L-proline (a) Substitution of di-n-pentylphosphinic acid [prepared as described in *J. Amer. Chem. Soc.* 77, 3411 (1955)] for dimethylphosphinic acid in the procedure of Example 10, part c, yields, di-n-pentylphosphinic acid, phenylmethyl ester.

(b) Substitution of di-n-pentylphosphinic acid, phenylmethyl ester for phenylmethylphosphinic acid, phenylmethyl ester in the procedure of Example 10, part d, yields 2-(pentyl(phenylmethoxy)phsophinyl)hexanoic acid.

(c) Substitution of 2-(n-pentyl(phenylmethoxy)phosphinyl)hexanoic acid for (phenyl(phenylmethoxy)phosphinyl]acetic acid in the procedure of Example 10, part e yields 1-[1-oxo-2-[pentyl(phenylmethoxy)phosphinyl]hexyl]-L-proline, phenylmethyl ester.

(d) Substitution of 1-[1-oxo-2-[pentyl(phenylmethoxy)phosphinyl]hexyl]-L-proline, phenylmethyl ester for 1-[[phenyl(phenylmethoxy)phosphinyl]acetyl]-L-proline, phenylmethyl ester in the procedure of Example 10, part f, yields 1-[2-(hydroxypentylphosphinyl)-1-oxohexyl]-L-proline.

What is claimed is:

1. A compound of the formula

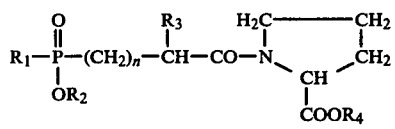

wherein $R_1$ is lower alkyl, phenyl or phenyl-lower alkyl;

$R_2$ is hydrogen, phenyl-lower alkyl or monovalent metal ion;

$R_3$ is hydrogen or lower alkyl;

$R_4$ is hydrogen, lower alkyl, phenyl-lower alkyl or monovalent metal ion; and n is 0 or 1.

2. A compound of claim 1 wherein the proline portion of the molecule is in the L-form.

3. A compound as in claim 2 wherein $R_4$ is hydrogen.

4. A compound as in claim 2 wherein n is 0.

5. A compound as in claim 2 wherein n is 1.

6. A compound as in claim 1 wherein $R_2$ and $R_4$ each is hydrogen.

7. A compound as in claim 1 wherein n is 0 or 1; $R_1$ is phenyl or phenyl-lower alkyl; $R_2$ is hydrogen or phenyl-lower alkyl; and $R_3$ is hydrogen or lower alkyl; and $R_4$ is hydrogen or alkali metal.

8. A compound in claim 4 wherein $R_1$ is 2-phenylethyl and $R_2$, $R_3$ and $R_4$ each is hydrogen.

9. A compound as in claim 4 wherein $R_1$ is 3-phenylpropyl and $R_2$, $R_3$ and $R_4$ each is hydrogen.

10. A compound as in claim 5 wherein $R_1$ is phenyl and $R_2$, $R_3$ and $R_4$ each is hydrogen.

11. A compound as in claim 4 wherein $R_1$ is phenyl and $R_2$, $R_3$ and $R_4$ each is hydrogen.

12. A compound as in claim 4 wherein $R_1$ is methyl and $R_2$, $R_3$ and $R_4$ each is hydrogen.

13. A compound as in claim 4 wherein $R_1$ is ethyl and $R_2$, $R_3$ and $R_4$ each is hydrogen.

14. A compound as in claim 4 wherein $R_1$ is butyl and $R_2$, $R_3$ and $R_4$ each is hydrogen.

15. A compound as in claim 4 wherein $R_1$ is phenyl, $R_2$ is 2-phenylethyl and $R_3$ and $R_4$ each is hydrogen.

16. A compound as in claim 5 wherein $R_1$ is methyl and $R_2$, $R_3$ and $R_4$ each is hydrogen.

17. A compound as in claim 5 wherein $R_1$ is phenyl, $R_3$ is methyl and $R_2$ and $R_4$ each is hydrogen.

18. A compound as in claim 4 wherein $R_1$ is phenylmethyl and $R_2$, $R_3$ and $R_4$ each is hydrogen.

19. A compound as in claim 4 wherein $R_1$ is phenylmethyl, $R_3$ is hydrogen, and $R_2$ and $R_4$ each is sodium.

20. A compound as in claim 4 wherein $R_1$ and $R_4$ each is 2-phenylethyl, and $R_2$ and $R_3$ each is hydrogen.

21. A compound as in claim 4 wherein $R_1$ is 3-phenylpropyl, $R_3$ is methyl, and $R_2$ and $R_4$ each is hydrogen.

22. A compound as in claim 4 wherein $R_1$ is phenyl, $R_2$ and $R_3$ each is hydrogen and $R_4$ is ethyl.

23. A compound as in claim 4 wherein $R_1$ is phenyl, $r_2$ and $R_4$ each is potassium and $R_3$ is hydrogen.

24. A compound as in claim 4 wherein $R_1$ is pentyl, $R_2$ and $R_4$ each is hydrogen and $R_4$ is butyl.

* * * * *

UNITED STATES PATENT AND TRADEMARK OFFICE
CERTIFICATE OF CORRECTION

PATENT NO. : 4,168,267
DATED : September 18, 1979
INVENTOR(S) : Edward W. Petrillo, Jr.

It is certified that error appears in the above—identified patent and that said Letters Patent is hereby corrected as shown below:

Col. 12, line 8, "dissopropylamine" should read
-- diisopropylamine --.
Col. 15, line 23, "pghosphinyl" should read
-- phosphinyl --.
Col. 16, line 8, 1-[2-(Hydroxyphenylphosphinyl) should read
-- 1-[2-(Hydroxypentylphosphinyl) --.
Col. 18, line 10 "$r_2$" should read -- $R_2$ --.

Signed and Sealed this

Twenty-first Day of October 1980

[SEAL]

Attest:

SIDNEY A. DIAMOND

Attesting Officer — Commissioner of Patents and Trademarks